United States Patent
Fernandez et al.

(10) Patent No.: US 9,551,026 B2
(45) Date of Patent: Jan. 24, 2017

(54) METHOD FOR NUCLEIC ACID DETECTION USING VOLTAGE ENHANCEMENT

(75) Inventors: Andres Fernandez, San Francisco, CA (US); Bryan Staker, Pleasanton, CA (US); Radoje Drmanac, Los Altos Hills, CA (US)

(73) Assignee: Complete Genomincs, Inc., Mountain View, CA (US)

( * ) Notice: Subject to any disclaimer, the term of this patent is extended or adjusted under 35 U.S.C. 154(b) by 0 days.

(21) Appl. No.: 13/337,968

(22) Filed: Dec. 27, 2011

(65) Prior Publication Data

US 2012/0122721 A1    May 17, 2012

Related U.S. Application Data

(62) Division of application No. 12/326,680, filed on Dec. 2, 2008.

(60) Provisional application No. 60/992,275, filed on Dec. 4, 2007, provisional application No. 60/992,039, filed on Dec. 3, 2007.

(51) Int. Cl.
  *C12Q 1/68* (2006.01)
(52) U.S. Cl.
  CPC ............ *C12Q 1/6832* (2013.01); *C12Q 1/6825* (2013.01)
(58) Field of Classification Search
  None
  See application file for complete search history.

(56) References Cited

U.S. PATENT DOCUMENTS

| | | |
|---|---|---|
| 4,284,897 A | 8/1981 | Sawamura et al. |
| 4,663,656 A | 5/1987 | Elabd et al. |
| 4,683,195 A | 7/1987 | Mullis et al. |
| 4,683,202 A | 7/1987 | Mullis |
| 4,800,159 A | 1/1989 | Mullis et al. |
| 4,883,750 A | 11/1989 | Whiteley et al. |
| 4,965,188 A | 10/1990 | Mullis et al. |
| 5,091,652 A | 2/1992 | Mathies et al. |
| 5,140,221 A | 8/1992 | Ichinose |
| 5,210,015 A | 5/1993 | Gelfand et al. |
| 5,296,700 A | 3/1994 | Kumagai |
| 5,381,224 A | 1/1995 | Dixon et al. |
| 5,399,491 A | 3/1995 | Kacian et al. |
| 5,424,413 A | 6/1995 | Hogan et al. |

(Continued)

FOREIGN PATENT DOCUMENTS

| | | |
|---|---|---|
| EP | 962772 A2 | 12/1999 |
| WO | WO 97/19193 A2 | 5/1997 |

(Continued)

OTHER PUBLICATIONS

Berg et al, Bioelectrochemistry and Bioengergetics, vol. 8, pp. 167-178 (1981).*

(Continued)

*Primary Examiner* — Robert T Crow
(74) *Attorney, Agent, or Firm* — Kilpatrick Townsend & Stockton LLP; Kenneth R. Allen; J. Michael Schiff

(57) ABSTRACT

Methods are provided for carrying out DNA sequencing on a device having upper and lower conductive layers separated by an insulative layer. Holes in the upper conductive layer create discrete attachment sites for DNA fragments. Voltage is applied to the surface to control affinity between the attachment sites and the DNA fragments, and to compact the DNA fragments for discrete optical detection.

24 Claims, 10 Drawing Sheets

Low voltage state

High voltage state

(56) References Cited

U.S. PATENT DOCUMENTS

| | | | |
|---|---|---|---|
| 5,426,180 A | 6/1995 | Kool | |
| 5,451,503 A | 9/1995 | Hogan et al. | |
| 5,466,348 A * | 11/1995 | Holm-Kennedy | 205/775 |
| 5,473,060 A | 12/1995 | Gryaznov et al. | |
| 5,476,930 A | 12/1995 | Letsinger et al. | |
| 5,504,336 A | 4/1996 | Noguchi | |
| 5,552,272 A | 9/1996 | Bogart | |
| 5,593,826 A | 1/1997 | Fung et al. | |
| 5,646,411 A | 7/1997 | Kain et al. | |
| 5,672,880 A | 9/1997 | Kain | |
| 5,834,758 A | 11/1998 | Trulson et al. | |
| 5,847,400 A | 12/1998 | Kain et al. | |
| 5,854,033 A | 12/1998 | Lizardi | |
| 5,871,921 A | 2/1999 | Landegren et al. | |
| 5,958,760 A | 9/1999 | Freeman | |
| 5,990,479 A | 11/1999 | Weiss et al. | |
| 6,008,892 A | 12/1999 | Kain et al. | |
| 6,174,670 B1 | 1/2001 | Wittwer et al. | |
| 6,177,990 B1 | 1/2001 | Kain et al. | |
| 6,207,392 B1 | 3/2001 | Weiss et al. | |
| 6,210,891 B1 | 4/2001 | Nyren et al. | |
| 6,251,303 B1 | 6/2001 | Bawendi et al. | |
| 6,253,303 B1 | 6/2001 | Shibuya | |
| 6,287,824 B1 | 9/2001 | Lizardi | |
| 6,306,597 B1 | 10/2001 | Macevicz | |
| 6,309,824 B1 | 10/2001 | Drmanac | |
| 6,319,426 B1 | 11/2001 | Bawendi et al. | |
| 6,322,901 B1 | 11/2001 | Bawendi et al. | |
| 6,396,995 B1 | 5/2002 | Stuelpnagel et al. | |
| 6,401,267 B1 | 6/2002 | Drmanac | |
| 6,403,376 B1 | 6/2002 | Toner et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,455,260 B1 | 9/2002 | Muller et al. | |
| 6,489,992 B2 | 12/2002 | Savoye | |
| 6,544,732 B1 | 4/2003 | Chee et al. | |
| 6,566,058 B1 | 5/2003 | Cardy | |
| 6,576,291 B2 | 6/2003 | Bawendi et al. | |
| 6,740,214 B1 | 5/2004 | Dobson et al. | |
| 6,815,167 B2 | 11/2004 | Crothers et al. | |
| 6,828,100 B1 | 12/2004 | Ronaghi | |
| 6,833,246 B2 | 12/2004 | Balasubramanian | |
| 6,864,052 B1 | 3/2005 | Drmanac et al. | |
| 6,867,048 B2 | 3/2005 | Kovacs | |
| 6,911,345 B2 | 6/2005 | Quake et al. | |
| 6,950,098 B2 | 9/2005 | Brabander et al. | |
| 6,960,437 B2 | 11/2005 | Enzelberger et al. | |
| 7,025,935 B2 | 4/2006 | Jones et al. | |
| 7,056,669 B2 | 6/2006 | Kayyem et al. | |
| 7,060,224 B2 | 6/2006 | Edman et al. | |
| 7,070,927 B2 | 7/2006 | Drmanac | |
| 7,101,717 B2 | 9/2006 | Kovacs | |
| 7,118,910 B2 | 10/2006 | Unger et al. | |
| 7,198,901 B1 | 4/2007 | Rachlin | |
| 7,216,291 B2 | 5/2007 | Kim | |
| 7,220,549 B2 | 5/2007 | Buzby | |
| 7,227,633 B2 | 6/2007 | Kraus et al. | |
| 7,244,559 B2 | 7/2007 | Rothberg et al. | |
| 7,264,929 B2 | 9/2007 | Rothberg et al. | |
| 7,327,349 B2 | 2/2008 | Robbins et al. | |
| 7,988,918 B2 | 8/2011 | Fernandez | |
| 8,287,812 B2 | 10/2012 | Fernandez | |
| 2002/0045045 A1 | 4/2002 | Adams et al. | |
| 2002/0045182 A1 | 4/2002 | Singh et al. | |
| 2002/0064795 A1 * | 5/2002 | Hashimoto | 435/6 |
| 2002/0102596 A1 * | 8/2002 | Davis | 435/6 |
| 2002/0132376 A1 | 9/2002 | Akimoto et al. | |
| 2003/0017264 A1 | 1/2003 | Treadway et al. | |
| 2003/0077642 A1 | 4/2003 | Fritsch et al. | |
| 2003/0096418 A1 | 5/2003 | Yamazaki et al. | |
| 2003/0156121 A1 | 8/2003 | Willis | |
| 2003/0156124 A1 | 8/2003 | Good et al. | |
| 2003/0161575 A1 | 8/2003 | Tu | |
| 2003/0162214 A1 * | 8/2003 | Heller et al. | 435/6 |
| 2004/0086892 A1 * | 5/2004 | Crothers et al. | 435/6 |
| 2004/0110213 A1 | 6/2004 | Namsaraev | |
| 2004/0132050 A1 | 7/2004 | Monforte | |
| 2004/0247485 A1 | 12/2004 | Kraus et al. | |
| 2005/0052646 A1 | 3/2005 | Wohlstadter et al. | |
| 2005/0112548 A1 | 5/2005 | Segawa et al. | |
| 2005/0156207 A1 | 7/2005 | Yazawa et al. | |
| 2005/0186590 A1 * | 8/2005 | Crothers et al. | 435/6 |
| 2005/0244456 A1 | 11/2005 | Nilsson et al. | |
| 2006/0014151 A1 | 1/2006 | Ogura et al. | |
| 2006/0024711 A1 | 2/2006 | Lapidus et al. | |
| 2006/0134657 A1 * | 6/2006 | Hodko et al. | 435/6 |
| 2006/0199193 A1 | 9/2006 | Koo et al. | |
| 2006/0270229 A1 | 11/2006 | Corderman et al. | |
| 2007/0087362 A1 | 4/2007 | Church et al. | |
| 2007/0099208 A1 | 5/2007 | Drmanac et al. | |
| 2007/0128610 A1 | 6/2007 | Buzby | |
| 2007/0188746 A1 | 8/2007 | Kraus et al. | |
| 2007/0207482 A1 | 9/2007 | Church et al. | |
| 2009/0130703 A1 | 5/2009 | Wagner et al. | |
| 2009/0155793 A1 | 6/2009 | Oliphant | |

FOREIGN PATENT DOCUMENTS

| | | |
|---|---|---|
| WO | WO 01/35088 A1 | 5/2001 |
| WO | WO 02/48691 A1 | 6/2002 |
| WO | 2004/106902 A1 | 12/2004 |
| WO | WO 2005/082098 A2 | 9/2005 |
| WO | WO 2006/073504 A2 | 7/2006 |

OTHER PUBLICATIONS

Allawi, H., et al., "Thermodynamics and NMR of Internal G•T Mismatches in DNA", Biochemistry, 1997, vol. 36, No. 34, pp. 10581-10594.

Baudisch, P., et al. "Halo: a Technique for Visualizing Off-Screen Locations", CHI 2003 Proceedings, Ft. Lauderdale, FL., Apr. 5-10, 2003, 8 pages. © 2003 ACM 1-58113-453-3/02/0004.

Gustafson, S., et al., "Wedge: Clutter-Free Visualization of Off-Screen Locations", CHI 2008 Proceedings, Displayful and Display-less, Florence, Italy, Apr. 5-10, 2008, pp. 787-796. © 2008 ACM 978-1-60558-011-1/08/04.

Gustafson, et al., "Comparing Visualizations for Tracking Off-Screen Moving Targets", CHI 2007 Work-in-Progress Proceedings, San Jose, CA, Apr. 28-May 3, 2007, pp. 2399-2404. © 2007 ACM 978-1-59593-642-4/07/0004.

Irani, P., et al., "Improving Selection of Off-Screen Targets with Hopping", CHI 2006 Proceedings Multidisplay Environments, Montréal, Québec, Canada, Apr. 22-27, 2006, pp. 299-308. © 2006 ACM 1-59593-178-3/06/0004.

Kricka, L. "Stains, Labels and Detection Strategies for Nucleic Acids Assays", Ann. Clin. Biochem., Association of Clinical Biochemists, 2002, vol. 39, pp. 114-129.

Margulies, M., et al., "Genome Sequencing in Microfabricated High-Density Picolitre Reactors", Nature, Sep. 15, 2005, vol. 437, pp. 376-380.

Ronaghi, M., et al., "Real-Time DNA Sequencing Using Detection of Pyrophosphate Release", Analytical Biochemistry, 1996, vol. 242, Article No. 0432, pp. 84-89.

Shendure, J., et al., "Accurate Multiplex Polony Sequencing of an Evolved Bacterial Genome", Science, Sep. 5, 2005, vol. 309, pp. 1728-1739.

Non-Final Office Action of Apr. 18, 2011 for U.S. Appl. No. 12/326,680, 20 pages.

Restriction Requirement of Feb. 24, 2011 for U.S. Appl. No. 12/326,680, 7 pages.

Beaucage, "Strategies in the Preparation of DNA Oligonucleotide Arrays for Diagnostic Applications," Current Medical Chemistry (2001) vol. 8, pp. 1213-1244.

J. Craig Venter Institute, Examples of human genome data [online]. http://www.jcvi.org/researchhuref/ [retrieved on Dec. 19, 2008].

National Center for Biotechnology Information, Examples of human genome data [online], [retrieved on Dec. 19, 2008]. Retrieved from the Internet <URL: http://www.ncbi.nlm.nih.gov/RefSeq/>.

(56) References Cited

OTHER PUBLICATIONS

Xu et al., "High sequence fidelity in a non-enzymatic DNA autoligation reaction," ©Oxford University Press Nucleic Acids Research, 1999, vol. 27, No. 3. pp. 875-881.
Non-Final Office Action of Feb. 8, 2012 for U.S. Appl. No. 12/333,575, 46 pages.
Final Office Action of Jan. 12, 2012 for U.S. Appl. No. 12/326,680, 30 pages.
Non-Final Office Action mailed on Aug. 5, 2014, for U.S. Appl. No. 12/326,680, 25 pages.
International Preliminary Report on Patentability mailed on May 4, 2010, for PCT Patent Application No. PCT/US/2008/082084, 5 pages.
Final Office Action dated Apr. 29, 2015 for U.S. Appl. No. 12/326,680, 27 pages.

\* cited by examiner

METHOD FOR NUCLEIC ACID DETECTION USING VOLTAGE ENHANCEMENT

CROSS-REFERENCES TO RELATED APPLICATIONS

The present application is a division of U.S. application Ser. No. 12/326,680, filed on Dec. 2, 2008, entitled "METHOD AND DEVICE FOR NUCLEIC ACID DETECTION USING VOLTAGE ENHANCEMENT," which claims benefit under 35 USC 119(e) of U.S. provisional Application Nos. 60/992,039 and 60/992,275, filed on Dec. 3, 2007 entitled "ARRAY STRUCTURES FOR NUCLEIC ACID DETECTION," the contents of which are incorporated herein by reference in their entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This present invention relates generally to electronic systems for carrying out nucleic acid sequencing.

Arrays are often used in the fields of molecular biology, biochemistry and other life sciences for analyzing biological molecules, including nucleic acids (DNA, RNA) and proteins (enzymes, antigens, etc.) that have been tagged or labeled for detection. Many different surface preparation methods exist for the creation of such arrays, although the majority of techniques currently in use for array construction are primarily chemical in nature. Photolithographic techniques are widely used in the many conventional technologies to pattern arrays of biological features (e.g., nucleic acids such as DNA or RNA) onto substantially planar surfaces.

For example, a biological array can be obtained by providing an array substrate that is chemically treated, for example with hexamethyldisilazane (HMDS), which is known to have a low affinity for biological molecules such as nucleic acids, coated with a photoresist layer, and by etching the surface to provide discrete areas with exposed HMDS. The surface can then be further modified to produce array features composed of an aminosilane such as aminopropyldimethylethoxysilane (APDMES), which gives rise to active amino groups at the surface. In aqueous solution, the amino group features of the APDMES protonate to form a positively charged surface which, through electrostatic charges, will attract any biological molecules such as DNA and RNA, which have negatively-charged phosphate backbones.

Such previously described arrays are created by processes that are chemical in nature and electronically passive, and thus they have a number of limitations. First, the loading of biological samples to the array is limited in efficiency, as the substrates are generally exposed to air and thus exposed to contaminants prior to the loading of the biological molecules. In addition, the attractive forces of the binding of the biological molecules to the surface cannot be varied, since the forces are limited to the fixed, initial amine density on the surface. Thus, the topological distribution of the molecules is fixed, and neither the position nor the relative size of the biological molecules can be varied following array construction.

DEFINITIONS

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), Genome Analysis: A Laboratory Manual Series (Vols. I-IV); Weiner, Gabriel, Stephens, Eds. (2007), Genetic Variation: A Laboratory Manual; Dieffenbach, Dveksler, Eds. (2003), PCR Primer: A Laboratory Manual; Bowtell and Sambrook (2003), DNA Microarrays: A Molecular Cloning Manual; Mount (2004), Bioinformatics: Sequence and Genome Analysis; Sambrook and Russell (2006, Condensed Protocols from Molecular Cloning: A Laboratory Manual; and Sambrook and Russell (2002), Molecular Cloning: A Laboratory Manual (all from Cold Spring Harbor Laboratory Press); Stryer, L. (1995) Biochemistry (4th Ed.) W.H. Freeman, New York N.Y.; Gait, "Oligonucleotide Synthesis: A Practical Approach" 1984, IRL Press, London; Nelson and Cox (2000), Lehninger, Principles of Biochemistry 3rd Ed., W.H. Freeman Pub., New York, N.Y.; and Berg et al. (2002) Biochemistry, 5th Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "an attachment site", unless the context dictates otherwise, refers to multiple such attachment sites, and reference to "a method for sequence determination" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

"Adaptor" refers to an engineered construct comprising "adaptor elements" where one or more adaptors may be interspersed within target nucleic acid in a library construct. The adaptor elements or features included in any adaptor vary widely depending on the use of the adaptors, but typically include sites for restriction endonuclease recognition and/or cutting, sites for primer binding (for amplifying the library constructs) or anchor primer binding (for sequencing the target nucleic acids in the library constructs), nickase sites, and the like. In some aspects, adaptors are engineered so as to comprise one or more of the following: 1) a length of about 20 to about 250 nucleotides, or about 40 to about 100 oligonucleotides, or less than about 60 nucleotides, or less than about 50 nucleotides; 2) features so as to be ligated to the target nucleic acid as two "arms"; 3) different and distinct anchor binding sites at the 5' and the 3' ends of the adaptor for use in sequencing of adjacent target nucleic acid; and 4) one or more restriction sites.

"Amplicon" means the product of a polynucleotide amplification reaction. That is, it is a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle dependant amplification and like reactions (see, e.g., U.S. Pat. Nos. 4,683,195; 4,965,188; 4,683,202; 4,800159; 5,210,015; 6,174,670; 5,399,491; 6,287,824 and 5,854,033; and US Pub. No. 2006/0024711).

"Circle dependant replication" or "CDR" refers to multiple displacement amplification of a double-stranded circular template using one or more primers annealing to the same strand of the circular template to generate products representing only one strand of the template. In CDR, no additional primer binding sites are generated and the amount of product increases only linearly with time. The primer(s) used may be of a random sequence (e.g., one or more random hexamers) or may have a specific sequence to select for amplification of a desired product. Without further modification of the end product, CDR often results in the creation of a linear construct having multiple copies of a strand of the circular template in tandem, i.e. a linear, concatamer of multiple copies of a strand of the template.

"Circle dependant amplification" or "CDA" refers to multiple displacement amplification of a double-stranded circular template using primers annealing to both strands of the circular template to generate products representing both strands of the template, resulting in a cascade of multiple-hybridization, primer-extension and strand-displacement events. This leads to an exponential increase in the number of primer binding sites, with a consequent exponential increase in the amount of product generated over time. The primers used may be of a random sequence (e.g., random hexamers) or may have a specific sequence to select for amplification of a desired product. CDA results in a set of concatameric double-stranded fragments.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Duplex" means at least two oligonucleotides or polynucleotides that are fully or partially complementary and which undergo Watson-Crick type base pairing among all or most of their nucleotides so that a stable complex is formed. The terms "annealing" and "hybridization" are used interchangeably to mean formation of a stable duplex. "Perfectly matched" in reference to a duplex means that the poly- or oligonucleotide strands making up the duplex form a double-stranded structure with one another such that every nucleotide in each strand undergoes Watson-Crick base pairing with a nucleotide in the other strand. A "mismatch" in a duplex between two oligonucleotides or polynucleotides means that a pair of nucleotides in the duplex fails to undergo Watson-Crick base pairing.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of less than about 1M, more usually less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the Tm for the specific sequence at a defined ionic strength and pH. Exemplary stringent conditions include a salt concentration of at least 0.01 M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of 30° C. are suitable for allele-specific probe hybridizations.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921.

"Microarray" or "array" refers to a solid phase support having a surface, preferably but not exclusively a planar or substantially planar surface, which carries an array of sites containing nucleic acids such that each site of the array comprises identical copies of oligonucleotides or polynucleotides and is spatially defined and not overlapping with other member sites of the array; that is, the sites are spatially discrete. The array or microarray can also comprise a non-planar structure with a surface such as a bead or a well. The oligonucleotides or polynucleotides of the array may be covalently bound to the solid support, or may be non-covalently bound. Conventional microarray technology is reviewed in, e.g., Schena, Ed. (2000), Microarrays: A Practical Approach (IRL Press, Oxford). As used herein, "random array" or "random microarray" refers to a microarray where the identity of the oligonucleotides or polynucleotides is not discernable, at least initially, from their location but may be determined by a particular operation on the array, such as by sequencing, hybridizing decoding probes or the like. See, e.g., U.S. Pat. Nos. 6,396,995; 6,544,732; 6,401,267; and 7,070,927; WO publications WO 2006/073504 and 2005/082098; and US Pub Nos. 2007/0207482 and 2007/0087362.

"Nucleic acid", "oligonucleotide", "polynucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Probe" means generally an oligonucleotide that is complementary to an oligonucleotide or target nucleic acid under investigation. Probes used in certain aspects of the claimed invention are labeled in a way that permits detection, e.g., with a fluorescent or other optically-discernable tag.

"Sequence determination" in reference to a target nucleic acid means determination of information relating to the sequence of nucleotides in the target nucleic acid. Such information may include the identification or determination of partial as well as full sequence information of the target nucleic acid. The sequence information may be determined with varying degrees of statistical reliability or confidence. In one aspect, the term includes the determination of the identity and ordering of a plurality of contiguous nucleotides in a target nucleic acid starting from different nucleotides in the target nucleic acid.

"Substrate" refers to a solid phase support having a surface, usually planar or substantially planar, which carries an array of sites for attachment of nucleic acid macromolecules such that each site of the array is spatially defined and not overlapping with other member sites of the array; that is, the sites are spatially discrete and optically resolvable. The nucleic acid macromolecules of the substrates of the invention may be covalently bound to the solid support, or may be non-covalently bound, i.e. through electrostatic forces. Conventional microarray technology is reviewed in, e.g., Schena, Ed. (2000), Microarrays: A Practical Approach (IRL Press, Oxford).

"Macromolecule" used in relation to a nucleic acid means a nucleic acid having a measurable three dimensional structure, including linear nucleic acid molecules with comprising secondary structures (e.g., amplicons), branched nucleic acid molecules, and multiple separate copies of individual with interacting structural elements, e.g., complementary sequences, palindromes, or other sequence inserts that cause three-dimensional structural elements in the nucleic acid.

"Target nucleic acid" means a nucleic acid from a gene, a regulatory element, genomic DNA, cDNA, RNAs including mRNAs, rRNAs, siRNAs, miRNAs and the like and fragments thereof. A target nucleic acid may be a nucleic acid from a sample, or a secondary nucleic acid such as a product of an amplification reaction.

As used herein, the term "Tm" is commonly defined as the temperature at which half of the population of double-stranded nucleic acid molecules becomes dissociated into single strands. The equation for calculating the Tm of nucleic acids is well known in the art. As indicated by standard references, a simple estimate of the Tm value may be calculated by the equation: $Tm=81.5+16.6(\log 10[Na+]) \ 0.41(\%[G+C])-675/n-1.0$ m, when a nucleic acid is in aqueous solution having cation concentrations of 0.5 M, or less, the (G+C) content is between 30% and 70%, n is the number of bases, and m is the percentage of base pair mismatches (see e.g., Sambrook J et al., "Molecular Cloning, A Laboratory Manual", 3rd Edition, Cold Spring Harbor Laboratory Press (2001)). Other references include more sophisticated computations, which take structural as well as sequence characteristics into account for the calculation of Tm (see also, Anderson and Young (1985), Quantitative Filter Hybridization, Nucleic Acid Hybridization, and Allawi and SantaLucia (1997), Biochemistry 36:10581-94).

In the following figures and figure descriptions, the numbering of various components of the substrates and devices comprising such substrates is retained for clarity; for example, conductive material is shown at 101 in FIG. 1, 201 in FIG. 2, 301 in FIG. 3, and so on.

SUMMARY OF THE INVENTION

The present invention provides methods for analysis of nucleic acid macromolecules. Specifically, the invention is directed to devices and methods for carrying out nucleic acid analysis, including sequence identification employing voltage and/or controlled electric charge to enhance operation. The invention provides devices comprising substrates for nucleic acid analysis, each substrate comprising the following: 1) a first electrically conductive layer forming a surface, b) a first electrically insulative layer of dielectric material disposed upon the first conductive layer; c) a second electrically conductive layer disposed upon the first insulative layer in a pattern to define discrete attachment sites for macromolecules on the first insulative layer, the second conductive layer provided with means for resisting affinity for the macromolecules to impede their attachment to sites on the second conductive layer; terminals for the first and second conductive layers for applying a voltage pattern between the first conductive layer and the second conductive layer to control affinity between the macromolecules and the discrete attachment sites.

In one aspect of the invention, each macromolecule comprises multiple copies of a single target nucleic acid. In a specific aspect of the invention, each macromolecule comprises multiple sequential copies of a single target nucleic acid (or fragment thereof) in a concatamer. In yet other aspects, the macromolecules comprise multiple copies of two or more target nucleic acids (or fragments thereof). In specific aspects, the macromolecules comprise multiple sequential copies of two or more target nucleic acids (or fragments thereof) in a concatamer. Preferably one macromolecule is bound per attachment site.

In a preferred aspect, the substrates and devices comprise a plurality of random, target nucleic acid macromolecules of undetermined sequence disposed on a substrate, wherein the nucleic acid molecules are attached at least in part via electrostatic charge.

The nucleic acid molecules ideally are placed on the substrate in a manner that provides very high density and optimizes discrete analysis of each individual nucleic acid constructs to increase the amount of data that can be obtained from analysis of nucleic acids at each discrete attachment site. In a preferred embodiment, the distance between the nucleic acid molecules provides discrete analysis at least 30% of the nucleic acid constructs, preferably at least 50% of the nucleic acid constructs, more preferably at least 70% of the nucleic acid constructs, and optimally at least 90% of the nucleic acid constructs.

In one specific aspect of the invention, the device of the invention used with the method provides a unipolar device comprising two terminals. Such device comprises a substantially planar substrate connected to a variable voltage supply, and a non-conducting planar structure that physically separated from said substrate surface, e.g., by air or a solution, to provide a spatially-limited region for interrogation of the nucleic acid macromolecules. The substrate of such device comprises: a conductive layer; a thin film provided on the conductive layer; a second conductive layer partially provided on the thin film surface, wherein the second conductive layer defines discrete attachment sites for nucleic acid macromolecules; and nucleic acid macromolecules disposed in the attachment sites defined in the first thin film. The variable voltage supply of the device is connected to the conductive layer of the substrate and grounded by attachment to the second conductive layer disposed on the first thin film. Optionally, a second thin film (e.g., a dielectric layer) is provided on the second conductive layer.

In a more specific aspect of the invention, the unipolar device used with the method comprises a substantially planar conducting substrate and a patterned conducting layer separated from the substrate by an insulating layer. The top surface of the conducting layer is generally covered with a thin film (e.g., a monolayer) of material that has an intrinsically low affinity for nucleic acids.

In another aspect of the invention, the device used with the method of the invention is a three-terminal device, with a planar surface comprising conductive material physically separated from the substrate surface, e.g., by air or a solution, to provide a spatially-limited region for interrogation of the nucleic acid macromolecules. The substrate of such device comprises: a first conductive layer; a thin film provided on the conductive layer; a second conductive layer partially provided on the thin film surface, wherein the second conductive layer defines discrete attachment sites for nucleic acid macromolecules; and nucleic acid macromolecules disposed on the attachment sites. A variable voltage supply of the device is connected to the conductive layer of the substrate and grounded by attachment to a second conductive layer. For this configuration of the invention, another voltage source is added between the conducting layer and the third electrode, e.g., through the use of the planar conductive surface. This configuration has advantages in construction, such as the driving forces for attracting the macromolecular nucleic acid constructs to the surface extend much farther from the surface and thus may result in a more efficient introduction of the nucleic acid constructs to the substrate surface. This device may also optionally comprise a second thin film provided on the second conductive layer.

In a preferred embodiment, the distance between the nucleic acid molecules provides discrete analysis at least 30% of the nucleic acid constructs, preferably at least 50% of the nucleic acid constructs, more preferably at least 70% of the nucleic acid constructs, and optimally at least 90% of the nucleic acid constructs.

In a specific aspect of the embodiment, the attachment sites on the conductive layer are between 30-1000 nm in width, and in a preferred aspect the attachment sites are 200-500 nm in width, even more preferably approximately 300 nm in width. In another specific aspect of the embodiment, the attachment sites in the electronic substrate are separated by a distance of between 0.5 to 10 μm, preferably between 1-3 μm.

In certain preferred aspects of the various embodiments, the dielectric thin film used in the invention includes, but is not limited to, the following materials: $SiO_2$, $TiO_2$, $Ta_2O_5$, $HfO_2$, $ZrO_2$, $MgO$, $Si_3N_4$, $MgF_2$ and $YF_3$.

In specific embodiments, the attachment sites are holes in the second conductive layer created by masking of the thin film and deposition of the conductive material to defined areas of the substrate. In other specific embodiments, deposition of the conductive material and etching can be used to create the attachment sites on the substrate surface. The nucleic acid macromolecules can be placed on the array in a manner that provides very high density and discrete analysis of the individual nucleic acid constructs. The nucleic acid molecules are ideally disposed within each discrete attachment site in a manner that provides very high density and discrete analysis of the individual nucleic acid constructs. In specific aspects, a single macromolecule is provided in each attachment site.

In certain aspects of the invention, the molecules are disposed on the substrate through other means (e.g., covalent attachment) as well as through electrostatic forces.

Thus, in specific aspects, the oxide layer on which the nucleic acid macromolecules are attached is derivatized to provide a chemical means for attachment of the nucleic acid macromolecules, e.g., means for covalent attachment of the nucleic acids to the surface. Thus, the nucleic acids are attached to the substrate surface via chemical means, and electrical charge can be utilized for specific aspects of the invention, e.g., in assays to remove complementary probe sequences or during substrate construction for the creation of additional substrates using a single "master substrate".

In certain aspects of the invention, the molecules are disposed on the substrate primarily through electrostatic forces. The native charge of molecules such as nucleic acids, with negatively-charged phosphate backbones, can be used to draw and keep. A stronger electric field may be used to provide enough binding force per attachment site and to hold a macromolecule that may be substantially larger than the attachment sites, thus providing an efficient prevention of binding two macromolecules to the same active site. In specific aspects, the invention provides arrays comprising single macromolecules occupying at least 80% of the attachment sites, at least 90% of the attachment sites, at least 95% of the attachment sites, or at least 97% of the attachment sites.

In specific aspects of the invention, the devices comprise electronically active substrates of single molecules disposed on a surface, where the single molecules each comprise a concatamer of at least one target nucleic acid. In another aspect, devices of the invention include substrates of random nucleic acid molecules disposed on a surface, where the molecules each comprise a concatamer of at least one target nucleic acid and at least one adaptor oligonucleotide. With regard to the above, in another aspect, nucleic acid concatamers are disposed in a planar array randomly distributed onto defined attachment sites. Preferably, in this aspect, each discrete region comprises a single molecule and each is surrounded by an inter-regional space that is substantially free of other single molecules.

In view of the foregoing, it will be appreciated that a substrate in accordance with the present invention provides for very precise control of the potentials/charges applied to the electrodes of the substrate. One advantage of the invention is that the voltage can be varied to provide enhanced assays, both in terms of efficiency of probe hybridization and for removal or "stripping" of probe following hybridization, including ligation. Within certain physical limitations, the degree of compactness of a nucleic acid macromolecule can be varied by applying certain techniques in the device construction process.

The invention also provides methods of identifying a nucleotide sequence of a nucleic acid macromolecule. In one aspect of the invention, the sequence is identified using a device of the invention which comprises a plurality of nucleic acid macromolecules disposed on a conductive substrate surface. These nucleic acid macromolecules are generally attached to the substrate surface through electrostatic forces.

Another aspect of the invention provides methods of identifying a nucleotide sequence of a nucleic acid macromolecule using a device of the invention which comprises a plurality of nucleic acid macromolecules disposed on a conductive substrate surface, where the macromolecules are attached to the substrate surface through use of one or more attachment elements. Probes or oligonucleotides that specifically bind to a known sequence can be used to determine the presence of a sequence in one or more nucleic acid macromolecules on the substrate surface. Generally, this reaction takes place with a positive charge on the conductive surface, i.e., at each attachment site. Following hybridization of the probes to the macromolecules, the positive charge can be reversed, and a negative charge is applied to the substrate surface to aid in the removal of the hybridized probes from the macromolecules, allowing the substrate surface to be analyzed multiple times.

In certain aspects of the invention, methods are provided for creating one or more replica substrates from a "master substrate". In this case, two substrates are used: 1) a master substrate and 2) a replica substrate, and a couplings to provide a pattern of voltages to each substrate for control in connection with hybridization, amplification, replication and ligation.

In certain embodiments, multiple replica arrays can be created by continually re-amplifying the nucleic acids of the master substrate to create double-stranded nucleic acids on the substrate, and repeating the methods of the invention.

In other aspects of the invention, methods are provided for identifying a nucleotide sequence of a nucleic acid macromolecule on a substrate of the invention comprising a plurality of nucleic acid macromolecules disposed on a conductive substrate surface.

In specific aspects as described above, the nucleic acids can be attached to the substrate surface via an attachment element. These methods can then provide using a negative charge on the substrate surface to relax the molecules and aid in removing the hybridized probes. This can be performed for both the use of a single group of probes, or for the use of two or more sets of probes to identify a nucleic acid sequence, e.g., using the cPAL methods as described in more detail herein. In specific embodiments in which multiple cycles of hybridization and detection are desirable, the positive charge on the substrate may be reversed to facilitate in removal of hybridized probe, and then reversed back to a positive charge to perform the hybridization reactions. A stronger positive charge is optionally used on the conductive substrate following each hybridization reaction to facilitate discrete analysis of each macromolecule on the substrate.

Preferably, the voltage is decreased or reversed in a manner that will allow sufficient relaxation of structural elements of the nucleic acid macromolecule, but will still provide for stable attachment of the molecule to the array surface. This may be performed by decreasing the positive charge or, in aspects of the invention in which the macromolecules are attached through means other than electrostatic forces, by the application of a negative charge to the attachment sites.

In view of the foregoing, it is an object of the present invention to provide an improved biologic electrode substrate for carrying out and controlling multi-step and multiplex reactions.

In another aspect, the invention includes kits for making the devices of the invention and methods for implementing applications of the devices of the invention, particularly for use in high-throughput analysis of one or more target nucleic acids.

These and other objects, advantages, and features of the invention will become apparent to those persons skilled in the art upon reading the details of the methods as more fully described below.

DETAILED DESCRIPTION OF THE INVENTION

The substrates of the present invention may comprise a plurality of electrically isolated regions on a substrate material, called attachment sites, in which individual nucleic acid macromolecules can be disposed. The electrical isolation of these active regions is typically accomplished by thermal oxidation of a conductive layer, e.g., silicon, titanium, aluminum, or another appropriate conductive layer, forming the active regions. These attachment sites can be associated with a single electrode, or with multiple electrodes to allow independent control of discrete portions of a substrate.

Figure 1:
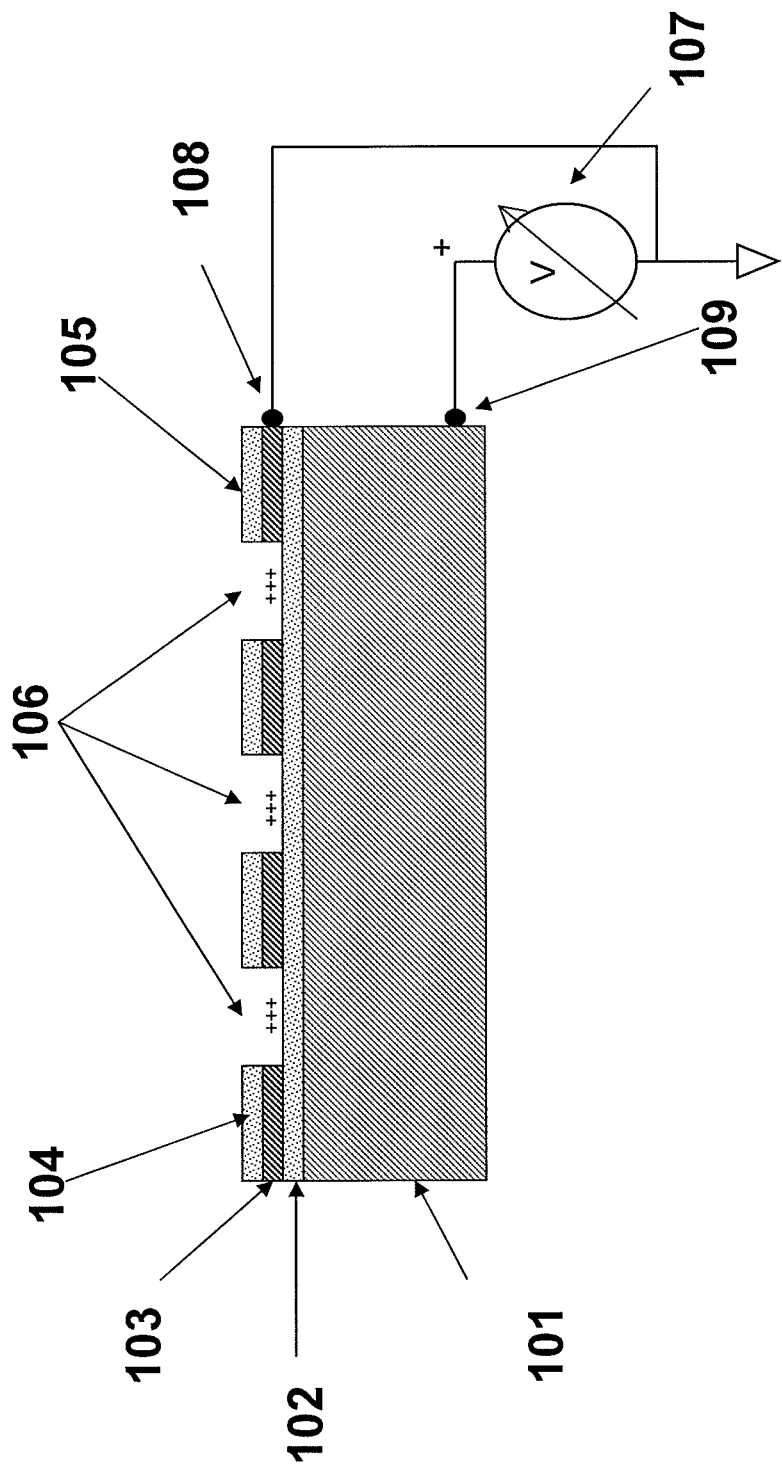
FIG. 1 is a schematic drawing illustrating a side view of a first general array substrate of the devices of the invention.

FIG. 1 is a schematic drawing illustrating a side view of a substrate for use in multiple embodiments of the invention. The substrate of this device comprises the specific elements: a conductive material 101, including but not limited to silicon, aluminum, titanium, or aluminum and/or titanium coated on silicon; a dielectric layer 102, such as an oxide disposed on the conductive layer, and in which there are a series of specific open regions or attachment sites 106, which serve as capture sites for the nucleic acid macromolecules to be analyzed, e.g., holes created by masking and deposition or holes created by deposition and etching ("attachment sites", raised regions surrounding the specific attachment sites comprising a second conductive layer 103 and a topside oxide layer 104, and terminals 108, 109 for coupling to a voltage supply 107. It is important that the top surface of the device 105 as is shown over layers 103 and 104 has low affinity to macromolecules. Dielectric materials for use in the substrates of devices of the invention include, but are not limited to, $SiO_2$, $TiO_2$, $Ta_2O_5$, $HfO_2$, $ZrO_2$, $MgO$, $Si_3N_4$, $MgF_2$ and $YF_3$. In specific embodiments, the dielectric layer is formed by selective oxidation of the conductive material (e.g., the top surface of an Si substrate can be oxidized to create an $SiO_2$ layer).

Figure 2:
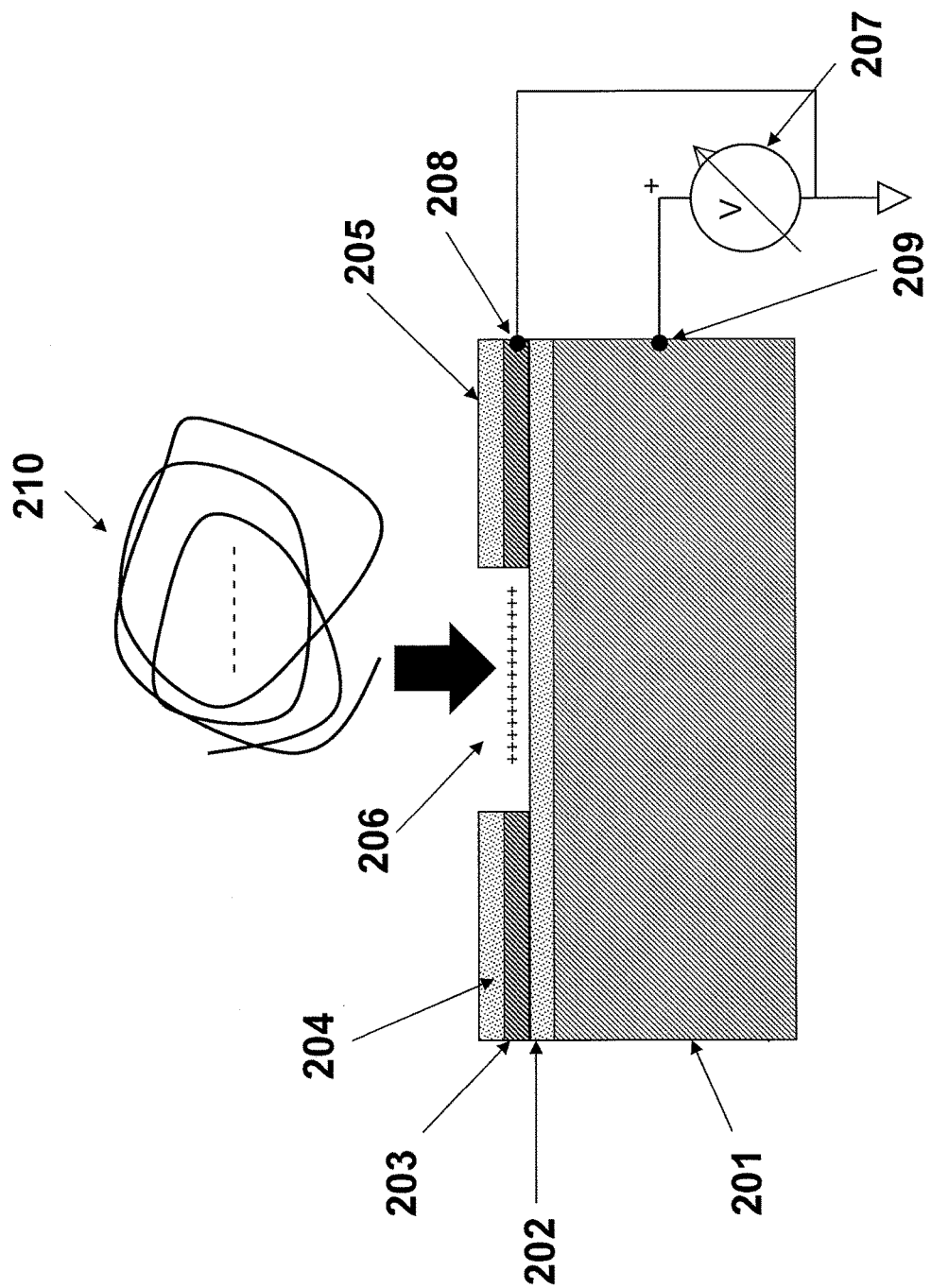
FIG. 2 is a schematic drawing illustrating the step of introducing a negatively-charged nucleic acid molecule to the array substrate structure of the devices of the invention.

FIG. 2 is a schematic drawing illustrating the step of introducing a negatively-charged nucleic acid molecule to a substrate of specific devices of the invention; e.g., an array of the invention, comprising a conductive material 201, a dielectric layer 202, attachment sites 206, raised regions surrounding the specific attachment sites comprising a second conductive layer 203 and a topside oxide layer 204, and a variable voltage supply 207 connected to a terminal 209 on the conductive layer 201 and grounded at a terminal 208 can be used to enhance binding of biological molecules to the conductive material at the attachment sites 206 through electrostatic forces. The voltage is applied in a pattern of duration and intensity to promote various aspects of operation, including enhanced affinity, enhanced compactness, relaxation of the macromolecules allowing expansion in size, and to promote release of attached macromolecules. A positive charge is applied to the conductive layer 201 that in turn positively charges the attachment sites 206, which then attract negatively-charged nucleic acid macromolecules such as DNA or RNA 210 to the discrete attachment sites. The top surface of the device is shown at 205 and is such as to resist affinity of the macromolecules. In specific aspects of the embodiments, the substrates of the invention can be constructed by introducing the nucleic acid constructs in solution to the substrate surface of an active electric support structure. A positive voltage is then applied to the array structure at sites 206 via substrate 201, which creates a net positive charge on the surface of the array substrate. Once the nucleic acid constructs are drawn to the attachment sites surface, continued application of voltage can keep the nucleic acids in place. However, short range forces such as Van der Waals forces also contribute to keeping the nucleic acid molecules on the surface of the array, allowing variation in the voltage over a limited range.

Figure 3:
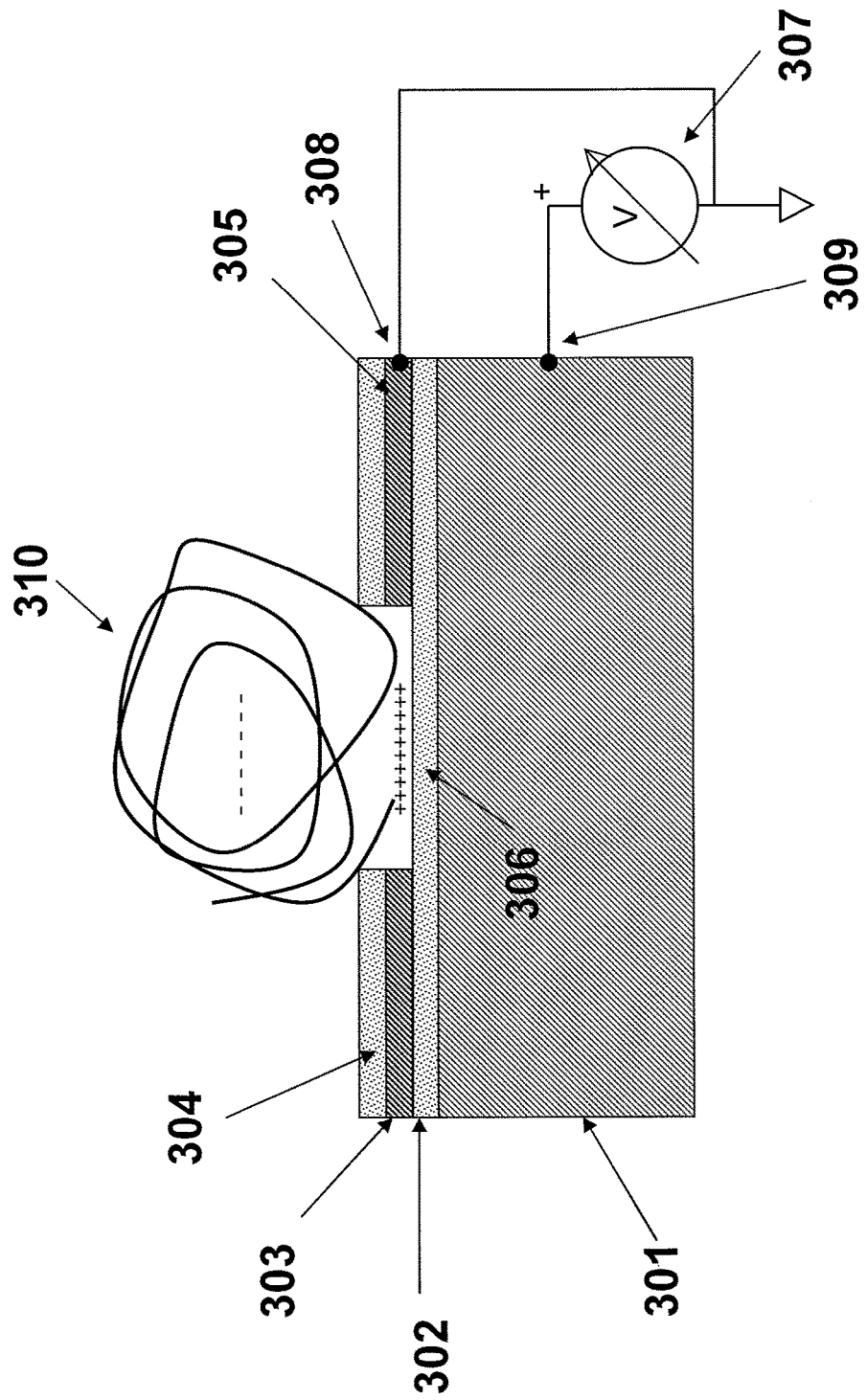
FIG. 3 is a schematic drawing illustrating the binding of the negatively-charged nucleic acid molecule to the array substrate structure of the devices of the invention.
Figure 4:
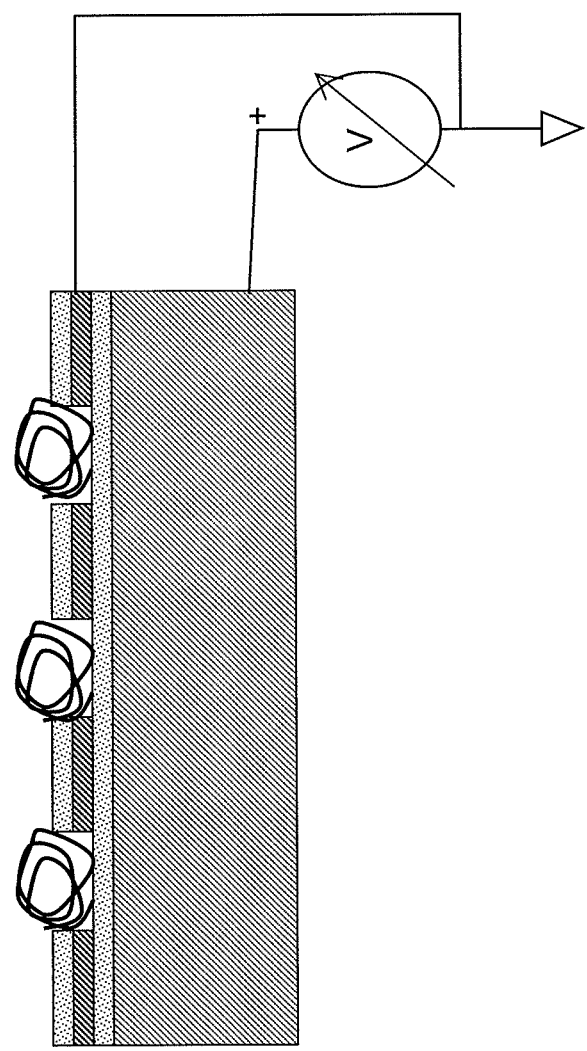
FIG. 4 is a schematic drawing illustrating a side view of a two terminal array of the devices of the invention.

FIG. 3 is a schematic drawing illustrating the bound negatively-charged nucleic acid macromolecule 310 attached to a substrate of the invention via a discrete attachment site 306. FIG. 4 shows a plurality of such molecules on a substrate in accordance with the invention.

Figure 5:
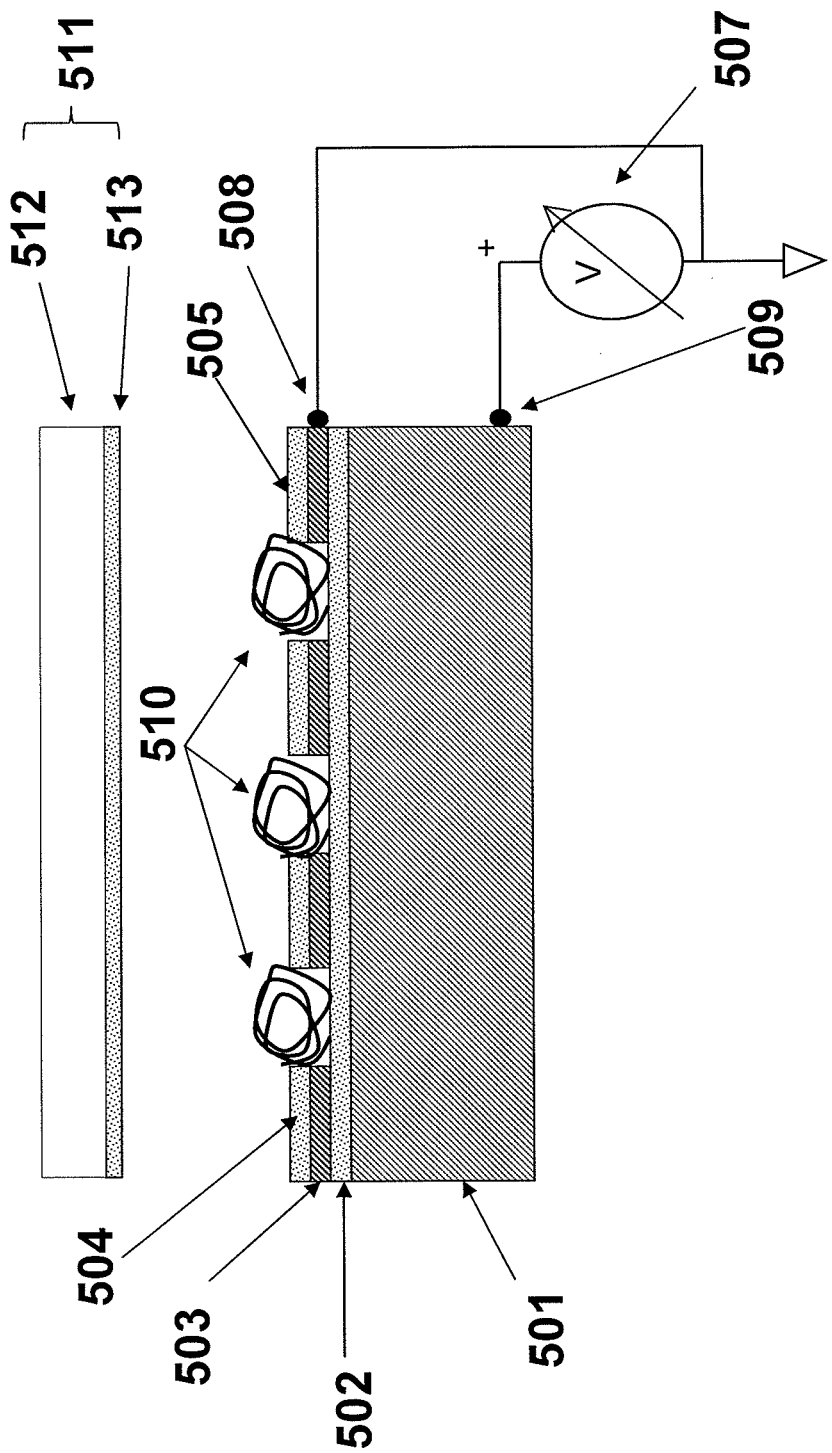
FIG. 5 is a schematic drawing illustrating a side view of a three terminal array of the devices of the invention.

FIG. 5 is a schematic drawing illustrating a side view of an example of a two terminal device of the invention. The substrate of the device comprises a conductive material 501, a dielectric layer 502, attachment sites 506, raised regions surrounding the specific attachment sites comprising a second conductive layer 503 and a topside oxide layer 504, and a variable voltage supply 507 connected to the conductive layer 509 and grounded by attachment to a shield 508. The voltage is applied in a pattern of duration and intensity to promote various aspects of operation, including enhanced affinity, enhanced compactness, relaxation of the macromolecules allowing expansion in size, and to promote release of attached macromolecules. A positive charge is applied to the conductive layer that then positively charges the attachment sites 506, which serves to attract negatively charged nucleic acid macromolecules such as DNA or RNA 510 to the discrete attachment sites. A non-conducting planar structure 511, here illustrated as comprising glass 512 and a transparent coating 513, e.g., indium tin oxide, is used to provide a spatially-limited region for interrogation of the nucleic acid macromolecules. The planar structure 511 is separated from the substrate surface by the space necessary for the delivery of the nucleic acid macromolecules to the substrate. The planar structure creates an enclosed or semi-enclosed region within which the biochemical reactions using the macromolecules of the invention can take place. The planar structure may be a conductive opaque material (e.g., a metal) that can be removed prior to analysis of the nucleic acid macromolecules; preferably, the planar structure provides optical availability for the detection of the biochemical interrogation reactions that take place on the substrate. Appropriate materials for such the planar structure include glass or plastic coated with a thin, transparent conductive coating, e.g., a thin layer of indium tin oxide.

The device created through the addition of the planar structure to the substrate can be substantially sealed, or may have an open region at one or both ends of the device for the introduction, removal and/or flow-through of any liquids, reagents, or other elements used for interrogation of the nucleic acid macromolecules.

Figure 6:
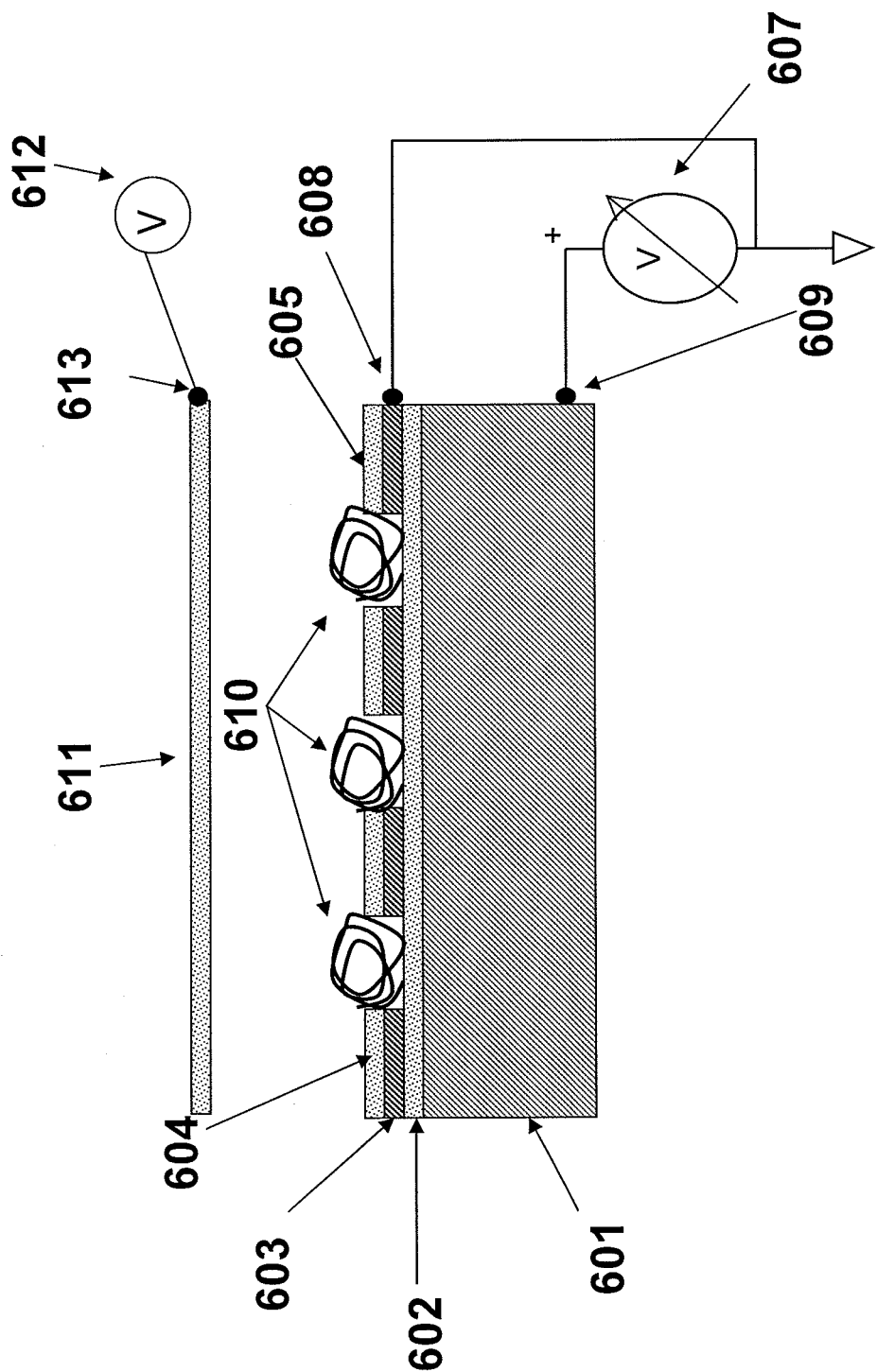
FIG. 6 is a schematic drawing illustrating the change in relative morphology of a negatively-charged nucleic acid molecule on an array of the invention following a change in voltage.

FIG. 6 is a schematic drawing illustrating a side view of a three terminal array of the devices of the invention. As with specific two terminal devices, the substrate of the device comprises a conductive material 601, a dielectric layer 602, attachment sites 606, raised regions surrounding the specific attachment sites comprising a second conductive layer 603 and a topside oxide layer 604, and a variable voltage supply 607 connected to the conductive layer 609 and grounded by attachment to a shield 608. The voltage is applied in a pattern of duration and intensity to promote various aspects of operation, including enhanced affinity, enhanced compactness, relaxation of the macromolecules allowing expansion in size, and to promote release of attached macromolecules. A positive charge is applied to the conductive layer of the device, which in turn positively charges the attachment sites 606, which serves to attract negatively charged nucleic acid macromolecules such as DNA or RNA 610 to the discrete attachment sites. A charge-bearing planar structure 611 may be positioned separately from the device by at least the space necessary for the analysis of the nucleic acid macromolecules, e.g., space for loading and/or extracting solutions or other reagents used with the device. The charge-bearing planar structure 611 in this aspect of the device comprises a conductive material attached to a second voltage supply 612 at attachment point 613 and referenced to ground or a common at terminal 608. The second voltage supply 612 may be fixed or variable. The device can be substantially sealed, or may have an open region at one or both ends of the device for the introduction, removal and/or flow-through of any liquids, reagents, or other elements used for interrogation of the nucleic acid macromolecules.

For the configuration of the substrates of the invention as described in FIG. 6, connections are provided for another voltage source that is added between the conducting layer and the third electrode. This configuration has advantages in construction, such as the provision of driving forces for attracting the macromolecular nucleic acid constructs to the surface that extend much farther from the surface and thus may result in a more efficient introduction of the nucleic acid constructs to the array surface.

Figure 7:
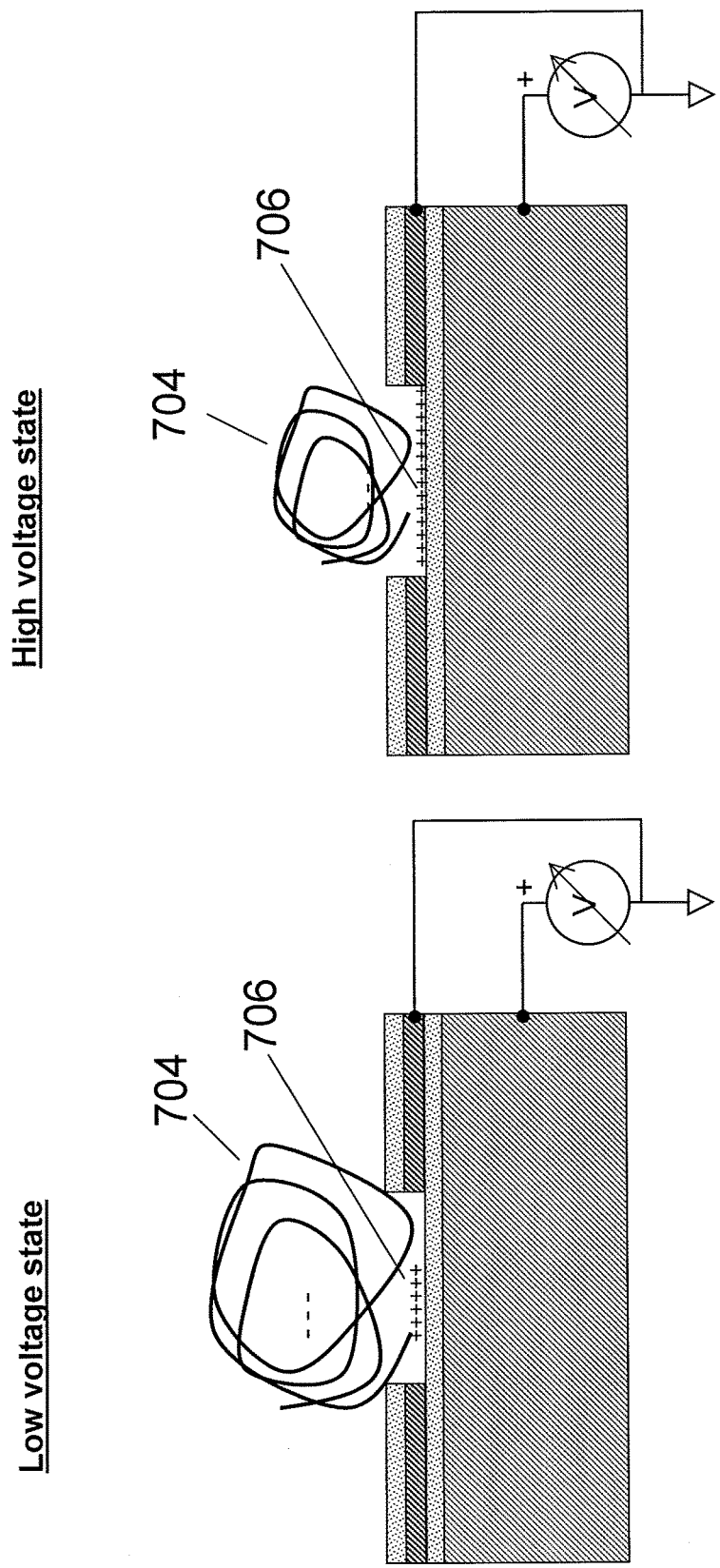
FIG. 7 is a schematic drawing illustrating the change in relative morphology of a negatively-charged nucleic acid molecule on an array of the invention following a change in voltage

FIG. 7 is a schematic drawing illustrating the change in relative morphology of a negatively-charged nucleic acid molecule on an array of the invention following a change in voltage. The strength of the positive charge on the attachment site can be varied by increasing the positive charge on the attachment surface 706 to "tighten" the nucleic acid macromolecule 704, or reducing the positive charge on the attachment surface 706 to relax the nucleic acid macromolecule 704. The relative charge is indicated by the plus signs at the attachment surface 706.

Device Construction

In specific embodiments, the devices of the invention are constructed using multi-layer coating technologies. The optimization of the multilayer coating design can be accomplished by application of techniques well known in the art. The attachment sites on the conductive layer base may be created, for example, by one of the following methods: thermal and/or electron beam vapor deposition, replication, transfer, film deposition, by processes of chemical vapor deposition (LPCVD, PECVD etc.) or of physical vapor deposition such as by sputtering, i.e., DC magnetron sputtering. Ion assisted deposition processes as well as sol-gel processes can be used as well. Alternatively, layers of substrate may be transferred onto the base by bonding or molecular adhesion.

In some aspects of constructing the device, etching is employed. Etching may be achieved by multiple available techniques, such as the damascene technique, whereby openings are selectively etched into a dielectric layer. Generally, a photoresist material is layered onto the dielectric layer and a pattern of openings is outlined in the photoresist layer using lithographic techniques. An anisotropic etch is then used to form the openings in the dielectric layer. The photoresist material is then removed. Where multiple layers and depths are desired, the use of more than one mask layer with varying resistances to the anisotropic etch processes may be employed. The photoresist patterning is preferably highly precise to enable accurate etching of the underlying layer.

Alternatively, or in addition to the use of electrostatic forces to attract and retain the nucleic acid macromolecules on the attachment sites, the nucleic acid macromolecules may be fixed to the discrete sites of the devices of the claimed invention by a variety of other techniques, including covalent attachment and non-covalent attachment of the nucleic acid macromolecules to the attachment sites. In one embodiment, the attachment sites may comprise attached capture oligonucleotides that form complexes, e.g., double-stranded duplexes, with a complementary segment of a nucleic acid macromolecules to be attached. In other embodiments, capture oligonucleotides may comprise oligonucleotide clamps, or like structures, that form triplexes with a segment of a nucleic acid macromolecule (see, e.g., U.S. Pat. No. 5,473,060). In another embodiment, the surface of the substrate may have reactive functionalities that react with complementary functionalities on the nucleic acid macromolecules to form a covalent linkage (see, e.g., Beaucage (2001), Current Medicinal Chemistry 8:1213-1244).

In very specific aspects of the embodiment, the nucleic acid macromolecular structures provided on the devices comprise DNA concatamers formed from multiple copies of one or more nucleic acid sequence. The construction of such molecules for introduction to the array substrates of the invention are disclosed, for example, in U.S. Pat. No. 20070099208, U.S. Pat. Nos. 6,815,167, 6,566,058, 5,451,503 and 5,424,413 and WO 97/19193. Certain of these describe methods of amplifying nucleic acid; e.g., by means of polymerase chain reaction (PCR), circle-dependent amplification (CDA), and like processes which produce long concatameric copies of nucleic acids.

In other aspects of the invention, certain configurations and methods of nucleic acid attachment can be used, e.g., to control the charge on specific subsets of attachments sites of the array of the invention or to facilitate in nucleic acid attachment. Examples of such configurations include those disclosed in U.S. Pat. No. 6,867,048, U.S. Pat. No. 7,056,669, U.S. Pat. No. 7,060,224, and U.S. Pat. No. 7,101,717, each of which are incorporated by reference herein.

Replica Substrates Comprising Nucleic Acids

The present invention can, in one specific aspect, be used to produce one or more identical substrates that comprise nucleic acid macromolecules complementary to a master substrate via replication or amplification and transfer of the replicated/amplified nucleic acid macromolecules to a separate array with substantially the same device structure, i.e., active electronic substrates with attachment sites spaced in the same manner as the master array.

In a specific aspects, the replica array may have uniform surface with no binding features and nonbinding areas.

Figure 8:
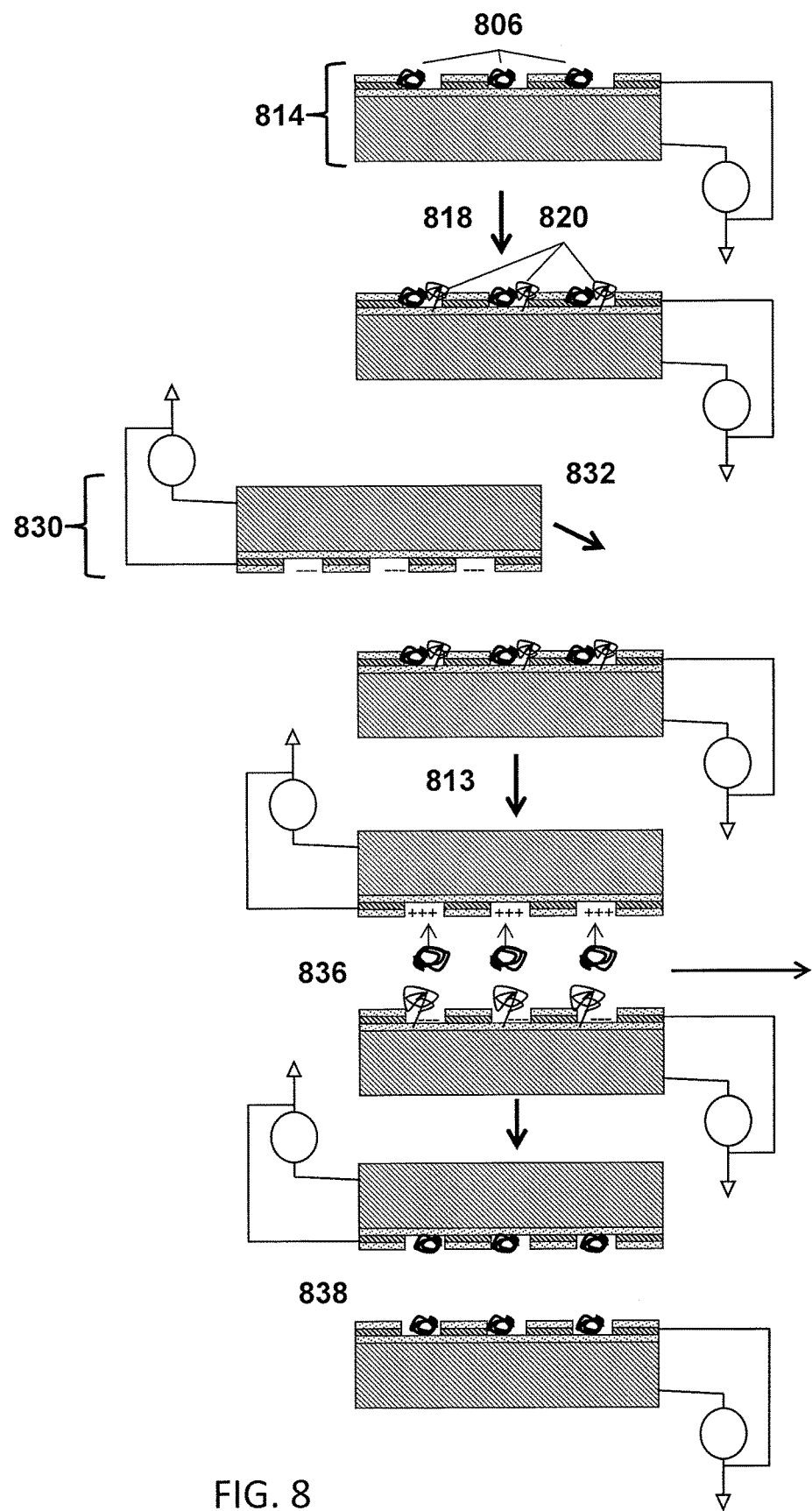
FIG. 8 is a schematic drawing illustrating the creation of a substrate of the invention from a master substrate.

Such a method is illustrated in FIG. 8. Here, a master substrate 814 comprising multiple, discrete, single-stranded nucleic acid macromolecules 806 is created using the methods as described herein, and in this particular aspect, the substrate contains the elements of FIG. 4. Each of the nucleic acid macromolecules 806 on the master substrate 814 is attached to the surface of the substrate using a second mechanism of attachment, e.g. a type of covalent or non-covalent binding ("attachment element"), in addition to binding by electrostatic forces. Each of the nucleic acid macromolecules is replicated or amplified (process 818) in the area of the attachment site to create nucleic acid copies that are complementary to each individual nucleic acid macromolecule 820. These copies are maintained in the area of their respective attachment sites due to hydrogen bonding or a positive charge that is applied to the conductive material of the substrate by the voltage supply. A replica substrate 830 is the introduced over the master substrate 814 comprising the replicated or amplified nucleic acid macromolecules 820 and positioned (in process 832) so that the attachment sites of the master substrate 814 are aligned with the desired attachment sites on the replica substrate 830. The voltage applied to each of the devices is then adjusted to attract the replicated/amplified nucleic acid macromolecules 820 from the master substrate 814 to the replica substrate 830 in process 834. By reducing the positive charge on the master substrate 814 (or in some instances providing a negative charge), and providing a stronger positive charge on the replica substrate 830, the replicated/amplified nucleic acid macromolecules 820 are attracted (in process 836) to the attachment sites on the replica substrate 830. The nucleic acid macromolecules 806 of the master substrate 814 will remain attached due to the secondary attachment elements. The end result 838 is two devices, a master substrate 814 with the master nucleic acid macromolecules 806 attached to attachment sites and a replica substrate 830 comprising replicated/amplified nucleic acid macromolecules 820 attached to attachment sites complementary to the nucleic acid macromolecules 806 attached to the master substrate 814. In certain instances, the replicated/amplified nucleic acid macromolecules 820 will be complementary to a specific fragment on the master nucleic acid macromolecule, depending on the replication/amplification methods used.

A master with hundreds of target nucleic acid copies per attachment site may be used to make multiple replica arrays, e.g., by limiting transfer to a fraction of available copies to one replica by controlling time and force. Nucleic acids on the replica array may be further in situ amplified to increase copy number per attachment site.

Methods of Use

Hybridization of probes on the substrates of the invention can be enhanced by using a lower positive voltage or introducing a negative voltage to the conductive surface—i.e., decreasing the positive charge on the array—which results in a more "relaxed", less densely packed nucleic acid macromolecule, providing greater access of the probes to the internal sequences in the nucleic acid macromolecule. In one aspect positive charge on the surface may be used to enhance delivery of probes or oligonucleotides to the attached macromolecules or to increase local concentration of oligonucleotides in the vicinity of attached macromolecules. On the other hand, for imaging purposes, it may be desirable to increase the positive charge to increase the density (yet decrease the size) of the nucleic acid macromolecules; i.e., to provide more "tightly packed" nucleic acid macromolecules. Use of these tightly packed macromolecules allows the use of arrays with higher density by providing more compact areas of signal and maintaining discrete analysis of each macromolecule. However, once the image (e.g., optical image) has been acquired, again it may be useful to decrease the voltage (i.e., the positive charge), again "relaxing" the nucleic acid macromolecules so that the bound probes are more easily stripped or separated from the nucleic acid macromolecules on the device.

Thus, using the devices of the claimed invention, voltage can be varied to provide the optimal nucleic acid macromolecule density for both imaging and for the hybridization, imaging and stripping techniques. Voltage can be used to reduce macromolecular density during probe hybridization and/or stripping techniques within a detection or sequencing process (e.g., by decreasing the positive charge on the device surface), and nucleic acid macromolecular density may then be increased following probe binding to provide a more compact nucleic acid macromolecule for detection purposes.

Figure 9:
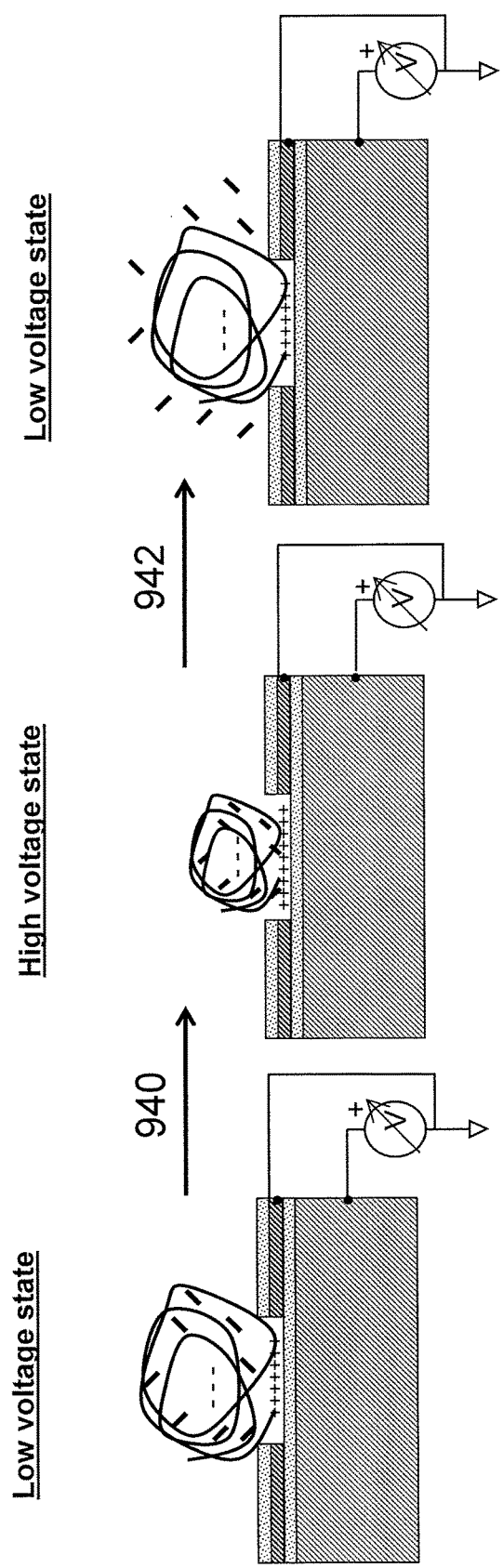
FIG. 9 is a schematic drawing illustrating the use in voltage changes in a hybridization reaction using a device of the invention.

As illustrated in FIG. 9, the positive charge on a device is decreased during hybridization 940 to increase access of the probes to the complementary nucleic acid macromolecule sequences. Following hybridization, the positive charge on the substrate surface is increased 942 to increase the density of the molecule and reduce its overall size, providing better discrete analysis of each molecule. Following imaging, where stripping of the probes is desired, the voltage can be once again decreased to reduce the positive charge, aiding the stripping process by "loosening up" or relaxing the probe-macromolecular duplexes. Following stripping of the probes from the substrate, as by a chemical process using a suitable chemical stripping agent in liquid solution, the substrate can be re-probed with another set of probes, either complementary to the same sequence as the first set of probes, e.g., to identify a different sequence from the first round of detection, or with the same probe set, e.g., to confirm the original data. For large-scale sequencing, the array can be probed with multiple probe sets to determine specific adjacent nucleic acids in each macromolecular nucleic acid structure.

Sequence Determination

In specific aspects of the invention, a variety of sequencing methodologies may be used to determine a sequence of the nucleic acid macromolecules using the devices of the invention, including but not limited to hybridization methods as disclosed in U.S. Pat. Nos. 6,864,052; 6,309,824; 6,401,267; sequencing-by-synthesis methods as disclosed in U.S. Pat. Nos. 6,210,891; 6,828,100, 6,833,246; 6,911,345; Margulies, et al. (2005), Nature 437:376-380 and Ronaghi, et al. (1996), Anal. Biochem. 242:84-89; and ligation-based methods as disclosed in U.S. Pat. No. 6,306,597; and Shendure et al. (2005) Science 309:1728-1739, to which reference is made for their teachings.

In one aspect, the nucleic acid macromolecules are used in sequencing by combinatorial probe-anchor ligation reaction (cPAL) (see U.S. Ser. No. 11/679,124, filed Feb. 24, 2007). In brief, cPAL comprises cycling of the following steps: First, an anchor is hybridized to a first adaptor in the DNBs (typically immediately at the 5' or 3' end of one of the adaptors). Enzymatic ligation reactions are then performed with the anchor to a fully degenerate probe population of, e.g., 8-mer probes that are labeled, e.g., with fluorescent dyes. Probes may have a length, e.g., about 6-20 bases, or, preferably, about 7-12 bases. At any given cycle, the population of 8-mer probes that is used is structured such that the identity of one or more of its positions is correlated with the identity of the fluorophore attached to that 8-mer probe. For example, when 7-mer sequencing probes are employed, a set of fluorophore-labeled probes for identifying a base immediately adjacent to an interspersed adaptor may have the following structure: 3'-F1-NNNNNNAp, 3'-F2-NNNNNNGp. 3'-F3-NNNNNNCp and 3'-F4-NNNNNNTp (where "p" is a phosphate available for ligation). In yet another example, a set of fluorophore-labeled 7-mer probes for identifying a base three bases into a target nucleic acid from an interspersed adaptor may have the following structure: 3'-F1-NNNNANNp, 3'-F2-NNNNGNNp. 3'-F3-NNNNCNNp and 3'-F4-NNNNTNNp. To the extent that the ligase discriminates for complementarity at that queried position, the fluorescent signal provides the identity of that base.

After performing the ligation and four-color imaging, the anchor:8-mer probe complexes are stripped and a new cycle is begun. With T4 DNA ligase, accurate sequence information can be obtained as far as six bases or more from the ligation junction, allowing access to at least 12 bp per adaptor (six bases from both the 5' and 3' ends), for a total of 48 bp per 4-adaptor DNB, 60 bp per 5-adaptor DNB and so on.

Figure 10:
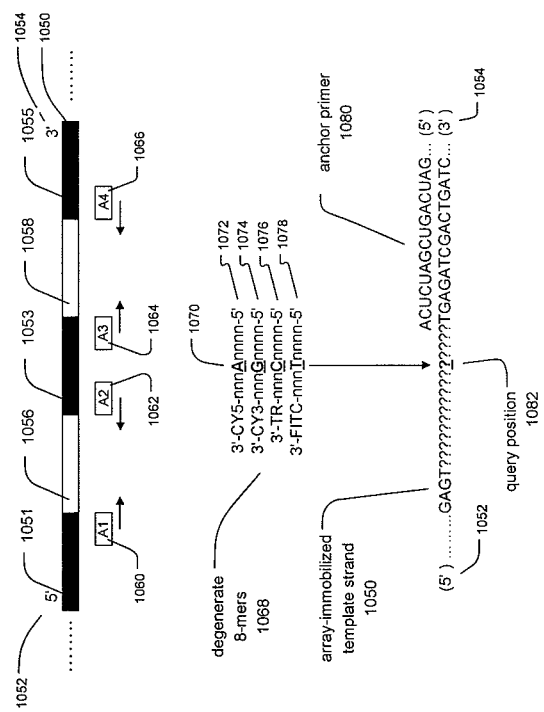
FIG. 10 is a schematic illustration of the components that may be used in an exemplary sequencing by combinatorial probe-anchor ligation technique (cPAL). Anchor 1080 (SEQ. ID NO:1) is hybridized to a complementary sequence (SEQ. ID NO:2) on the construct 1050 adjacent to the query position 1082, which is then interrogated with nucleic acid probes 1068.

FIG. 10 is a schematic illustration of the components that may be used in an exemplary sequencing by combinatorial probe-anchor ligation technique (cPAL). A construct 1050 is shown with two segments of target nucleic acid to be analyzed interspersed with three adaptors, with the 5' end of the stretch shown at 1052 and the 3' end shown at 1054. The target nucleic acid portions are shown at 1056 and 1058, with adaptor 1 shown at 1051, adaptor 2 shown at 1053 and adaptor 3 shown at 1055. Four anchors are shown: anchor A1 1060, which binds to the 3' end of adaptor 1 1051 and is used to sequence the 5' end of target nucleic acid 1056; anchor A2 1062, which binds to the 5' end of adaptor 2 1053 and is used to sequence the 3' end of target nucleic acid 1056; anchor A3 1064, which binds to the 3' end of adaptor 2 1053 and is used to sequence the 5' end of target nucleic acid 1058; and anchor A4 1066, which binds to the 5' end of adaptor 3 1055 and is used to sequence the 3' end of target nucleic acid 1058.

Depending on which position that a given cycle is aiming to interrogate, the 8-mer probes are structured differently. Specifically, a single position within each 8-mer probe is correlated with the identity of the fluorophore with which it is labeled. Additionally, the fluorophore molecule is attached to the opposite end of the 8-mer probe relative to the end targeted to the ligation junction. For example, in the graphic shown here, the anchor 1080 (SEQ. ID NO:1) is hybridized to a complementary sequence (SEQ. ID NO:2) on the construct 1050 such that its 3' end is adjacent to the target nucleic acid. To query a position five bases into the target nucleic acid, a population of degenerate 8-mer probes shown here at 1068 may be used. The query position is shown at 1082. In this case, this correlates with the fifth nucleic acid from the 5' end of the 8-mer probe, which is the end of the 8-mer probe that will ligate to the anchor. In the aspect shown in FIG. 10, the 8-mer probes are individually labeled with one of four fluorophores, where a fluorophore of Cy5 is correlated with A 1072, Cy3 is correlated with G 1074, Texas Red is correlated with C 1076, and FITC is correlated with T 1078.

Many different variations of cPAL or other sequencing-by-ligation approaches may be selected depending on various factors such as the volume of sequencing desired, the type of labels employed, the number of different adaptors used within each library construct, the number of bases being queried per cycle, how the DNBs are attached to the surface of the array, the desired speed of sequencing operations, signal detection approaches and the like. In the aspect shown in FIG. 10 and described herein, four fluorophores were used and a single base was queried per cycle. It should, however, be recognized that eight or sixteen fluorophores or more may be used per cycle, increasing the number of bases that can be identified during any one cycle.

The degenerate probes (in FIG. 10, the 8-mer probes) can be labeled in a variety of ways, including the direct or indirect attachment of radioactive moieties, fluorescent moieties, colorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka (2002), Ann. Clin. Biochem., 39: 114-129; and Haugland (2006), Handbook of Fluorescent Probes and Research Chemicals, 10th Ed. (Invitrogen/Molecular Probes, Inc., Eugene); Keller and Manak (1993), DNA Probes, 2nd Ed. (Stockton Press, New York, 1993); and Eckstein (1991), Ed., Oligonucleotides and Analogues: A Practical Approach (IRL Press, Oxford); and the like.

In one aspect, one or more fluorescent dyes are used as labels for the oligonucleotide probes. Labeling can also be carried out with quantum dots, as disclosed in the following patents and patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. Commercially available fluorescent nucleotide analogues readily incorporated into the degenerate probes include, for example, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red, the Cy fluorophores, the Alexa Fluor® fluorophores, the BODIPY® fluorophores and the like. FRET tandem fluorophores may also be used. Other suitable labels for detection oligonucleotides may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr) or any other suitable label.

Imaging acquisition may be performed by methods known in the art, such as use of the commercial imaging package Metamorph. Data extraction may be performed by a series of binaries written in, e.g., C/C++, and base-calling and read-mapping may be performed by a series of Matlab and Perl scripts. As described above, for each base in a target nucleic acid to be queried (for example, for 12 bases, reading 6 bases in from both the 5' and 3' ends of each target nucleic acid portion of each DNB), a hybridization reaction, a ligation reaction, imaging and a primer stripping reaction is performed. To determine the identity of each DNB in an array at a given position, after performing the biological sequencing reactions, each field of view ("frame") is imaged with four different wavelengths corresponding to the four fluorescent, e.g., 8-mers used. All images from each cycle are saved in a cycle directory, where the number of images is 4× the number of frames (for example, if a four-fluorophore technique is employed). Cycle image data may then be saved into a directory structure organized for downstream processing.

Data extraction typically requires two types of image data: bright field images to demarcate the positions of all DNBs in the array; and sets of fluorescence images acquired during each sequencing cycle. The data extraction software identifies all objects with the brightfield images, then for each such object, computes an average fluorescence value for each sequencing cycle. For any given cycle, there are four data-points, corresponding to the four images taken at different wavelengths to query whether that base is an A, G, C or T. These raw base-calls are consolidated, yielding a discontinuous sequencing read for each DNB. The next task is to match these sequencing reads against a reference genome.

Information regarding the reference genome may be stored in a reference table. A reference table may be compiled using existing sequencing data on the organism of choice. For example human genome data can be accessed through the National Center for Biotechnology Information at ftp.ncbi.nih.gov/refseq/release, or through the J. Craig Venter Institute at http://www.jcvi,org/researchhuref/. All or a subset of human genome information can be used to create a reference table for particular sequencing queries. In addition, specific reference tables can be constructed from empirical data derived from specific populations, including genetic sequence from humans with specific ethnicities, geographic heritage, religious or culturally-defined populations, as the variation within the human genome may slant the reference data depending upon the origin of the information contained therein.

In an alternative aspect of the claimed invention, parallel sequencing of the target nucleic acids in the DNBs on a random array is performed by combinatorial sequencing-by-hybridization (cSBH), as disclosed by Drmanac in U.S. Pat. Nos. 6,864,052; 6,309,824; and 6,401,267. In one aspect, first and second sets of oligonucleotide probes are provided, where each set has member probes that comprise oligonucleotides having every possible sequence for the defined length of probes in the set. For example, if a set contains probes of length six, then it contains 4096 (46) probes. In another aspect, first and second sets of oligonucleotide probes comprise probes having selected nucleotide sequences designed to detect selected sets of target polynucleotides. Sequences are determined by hybridizing one probe or pool of probes, hybridizing a second probe or a second pool or probes, ligating probes that form perfectly matched duplexes on their target nucleic acids, identifying those probes that are ligated to obtain sequence information about the target nucleic acid sequence, repeating the steps until all the probes or pools of probes have been hybridized, and determining the nucleotide sequence of the target nucleic acid from the sequence information accumulated during the hybridization and identification processes.

In yet another alternative aspect, parallel sequencing of the target nucleic acids in the DNBs is performed by sequencing-by-synthesis techniques as described in U.S. Pat. Nos. 6,210,891; 6,828,100, 6,833,246; 6,911,345; Margulies, et al. (2005), Nature 437:376-380 and Ronaghi, et al. (1996), Anal. Biochem. 242:84-89. Briefly, modified pyrosequencing, in which nucleotide incorporation is detected by the release of an inorganic pyrophosphate and the generation of photons, is performed on the DNBs in the array using sequences in the adaptors for binding of the primers that are extended in the synthesis.

Kits of the Invention

Kits for applications of arrays of the invention include, but are not limited to, kits for determining the nucleotide sequence of a target polynucleotide, kits for large-scale identification of differences between reference DNA sequences and test DNA sequences, kits for profiling exons, kits for creating replica substrates and the like. A kit typically comprises at least one support having a surface and one or more reagents necessary or useful for constructing a substrate of the invention, reagents for creating one or more replicas of a substrate, or for carrying out an application therewith. Certain kits comprise, in general, at least one substrate that can be associated with a reversible voltage supply, and reagents for the creation and use of substrates of the invention. Such reagents include, without limitation, nucleic acid primers, probes, adaptors, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In still another aspect, the invention provides kits for constructing a single molecule array comprising the following components: (i) a substrate of the invention; and (ii) a plurality of macromolecular structures, each having a unique functionality and multiple complementary functionalities, the macromolecular structures being capable of being attached randomly on the surface. In some aspects of such kits, the variable voltage supply is also provided, while in other aspects the kit is adapted for use with existing, commercially available voltage supplies.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

What is claimed is:

1. A method of discrete analysis of individual nucleic acid constructs in an array, said method comprising:
 (a) providing a device comprising a substrate comprising a surface and a plurality of nucleic acid macromolecules disposed on the surface at localized discrete attachment sites;
 (b) hybridizing a probe of known sequence having an optically detectable label to each of at least some of the nucleic acid macromolecules under conditions that permit formation of perfectly matched duplexes between the probe and complementary sequences in the nucleic acid macromolecules;
 (c) applying a positive charge to the substrate surface to promote compacting of the macromolecules for discrete optical detection; and
 (d) optically detecting the labeled duplexes while the positive voltage is applied, thereby identifying a nucleotide sequence in at least some of the nucleic acid macromolecules.

2. The method according to claim 1, comprising:
 hybridizing an oligonucleotide anchor to at least some of the nucleic acid macromolecules;
 hybridizing a probe of known sequence to each of at least some of the nucleic acid macromolecules at a position that is adjacent to an oligonucleotide anchor under conditions that permit formation of perfectly matched duplexes between the probes and complementary sequences in the nucleic acid macromolecules; and
 ligating at least some of the probes to an oligonucleotide anchor hybridized at an adjacent position.

3. The method according to claim 1, further comprising applying a negative voltage to the substrate surface to promote relaxation of the nucleic acid macromolecules; and then removing the probes from the nucleic acid macromolecules.

4. The method according to claim 1, wherein the nucleic acid macromolecules are singly disposed on the substrate surface at the localized discrete attachment sites that are separated by a distance of 0.3 µm to 10 µm.

5. The method of claim 1, wherein at least 80% of the localized discrete attachment sites are occupied by a single nucleic acid macromolecule, and the positive voltage compacts each nucleic acid macromolecule into its own discrete attachment site.

6. The method of claim 5, wherein the single nucleic acid macromolecules occupying at least 80% of the localized discrete attachment sites are amplicons.

7. The method of claim 1, wherein said probes of known sequence are each labeled with a fluorescent tag, and probes hybridized to the nucleic acid macromolecules are identified in step (d) by detecting fluorescence.

8. The method of claim 1, wherein the device comprises a dielectric layer disposed between two conductive layers, and the positive voltage is applied in step (c) between the two conductive layers.

9. The method of claim 8, wherein the substrate surface is a dielectric layer disposed on the lower conductive layer.

10. The method of claim 8, wherein the discrete attachment sites are defined areas of the substrate surface exposed through holes etched in the upper conductive layer, and wherein a topside layer that resists binding of nucleic acid macromolecules is disposed upon the upper conductive layer.

11. The method of claim 8, wherein one of the two conductive layers is a single layer below the surface, and the other layer is a single layer above the surface with openings around the discrete attachment sites,
 whereby the positive voltage is applied to the discrete attachment sites by applying a voltage between the two conductive layers.

12. A method of preparing nucleic acid macromolecules in an array, said method comprising:
 providing a device comprising a substrate comprising a surface and a plurality of nucleic acid macromolecules to be analyzed singly disposed on the surface at localized discrete attachment sites, said substrate surface having a positive electric charge at the discrete attachment sites;
 reducing but not removing the positive charge on the discrete attachment sites so as to relax the attached macromolecules in preparation for hybridizing probes of known sequence to the nucleic acid macromolecules at the attachment sites; and
 hybridizing the probes to the nucleic acid macromolecules under conditions that permit formation of perfectly matched duplexes between the probes and complementary sequences in the nucleic acid macromolecules; and
 compacting the nucleic acid molecules by increasing the positive charge on the discrete attachment sites after hybridizing the probes,
 wherein hybridization of each probe is indicative of a sequence in the nucleic acid macromolecule to which it is hybridized.

13. The method of claim 12 further comprising removing the probes from the nucleic acid macromolecules.

14. The method of claim 12, wherein at least 80% of the localized discrete attachment sites are occupied by a single nucleic acid macromolecule, and the positive charge compacts each nucleic acid macromolecule into its own discrete attachment site.

15. The method of claim 12, wherein the positive electric charge results from applying voltage between a lower conductive layer beneath the substrate surface and an upper conductive layer surrounding the attachment sites, wherein the device comprises a dielectric layer disposed between two conductive layers, and the positive electric charge results from applying voltage between the two conductive layers.

16. The method of claim 15, wherein at least 80% of the localized discrete attachment sites are occupied by a single nucleic acid macromolecule, and the positive electric charge compacts each nucleic acid macromolecule into its own discrete attachment site.

17. The method of claim 15, wherein one of the two conductive layers is a single layer below the surface, and the other layer is a single layer above the surface with openings around the discrete attachment sites, whereby the positive voltage is applied to the discrete attachment sites by applying a voltage between the two conductive layers.

18. The method of claim 12, wherein the discrete attachment sites are 30 nm to 1000 nm in size.

19. The method of claim 12, wherein the discrete attachment sites are 200 nm to 500 nm in size.

20. A method of compacting individual nucleic acid constructs in an array for discrete analysis, said method comprising:

providing a device comprising a plurality of different nucleic acid macromolecules to be analyzed that are singly disposed on a substrate surface at localized discrete attachment sites that are separated by a distance of 0.3 µm to 10 µm;

hybridizing labeled probes of known sequence to the nucleic acid macromolecules under conditions that permit formation of perfectly matched duplexes between the probes and complementary sequences in the nucleic acid macromolecules, wherein hybridization of the probe is indicative of a sequence in the nucleic acid macromolecule(s) to which it is hybridized;

applying a positive voltage to the substrate surface after hybridizing the probes such that the nucleic acid macromolecules are compacted for discrete analysis.

21. The method of claim 20, wherein at least 80% of the localized discrete attachment sites are occupied by a single nucleic acid macromolecule, and the positive charge compacts each nucleic acid macromolecule into its own discrete attachment site.

22. The method of claim 20, wherein the device comprises a dielectric layer disposed between two conductive layers, and the positive voltage is applied between the two conductive layers.

23. The method of claim 22, wherein one of the two conductive layers is a single layer below the surface, and the other layer is a single layer above the surface with openings around the discrete attachment sites, whereby the positive voltage is applied to the discrete attachment sites by applying a voltage between the two conductive layers.

24. The method of claim 20, wherein the discrete attachment sites are 30 nm to 500 nm in size.

* * * * *

UNITED STATES PATENT AND TRADEMARK OFFICE
CERTIFICATE OF CORRECTION

PATENT NO.        : 9,551,026 B2
APPLICATION NO.   : 13/337968
DATED             : January 24, 2017
INVENTOR(S)       : Andres Fernandez, Bryan P. Staker and Radoje Drmanac Page 1 of 1

It is certified that error appears in the above-identified patent and that said Letters Patent is hereby corrected as shown below:

On the Title Page

Column 1, Item (73), Assignee:
Delete "Complete Genomincs, Inc., Mountain View, CA (US)"
Add -- Complete Genomics, Inc., Mountain View, CA (US) --

Signed and Sealed this
Ninth Day of May, 2017

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 15
<212> TYPE: RNA
<213> ORGANISM: Artificial Sequence
<220> FEATURE:
<223> OTHER INFORMATION: Synthetic polynucleotide

<400> SEQUENCE: 1
gaucagucga ucuca                                                     15
```

```
<210> SEQ ID NO 2
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Query sequence of nucleotides of indeterminant
      length

<400> SEQUENCE: 2
tgagatcgac tgatc                                                     15
```